United States Patent [19]
Guttag

[11] Patent Number: 5,766,928
[45] Date of Patent: Jun. 16, 1998

[54] METHOD OF ELIMINATING HYDROCARBONS CONTAMINATING A REGION SUBJECTED TO EXTREME TEMPERATURES

[76] Inventor: Alvin Guttag, 6612 Whittier Blvd., Bethesda, Md. 20817

[21] Appl. No.: 487,158

[22] Filed: Jun. 7, 1995

Related U.S. Application Data

[60] Division of Ser. No. 224,718, Apr. 8, 1994, abandoned, which is a continuation-in-part of Ser. No. 853,428, Mar. 18, 1992, Pat. No. 5,346,929, which is a division of Ser. No. 486,217, Feb. 28, 1990, Pat. No. 5,120,089.

[51] Int. Cl.$^6$ .................................................. C07C 3/34
[52] U.S. Cl. ................ 435/262; 435/271; 435/281; 210/747; 210/922; 166/246
[58] Field of Search .................... 435/271, 281, 435/262; 210/747, 922; 166/246

[56] References Cited

U.S. PATENT DOCUMENTS

| | | |
|---|---|---|
| 656,435 | 8/1900 | Bonhoeffer. |
| 1,122,201 | 12/1914 | Hiemenz. |
| 1,338,297 | 4/1920 | Gruttefien. |
| 1,689,696 | 10/1928 | Summers. |
| 4,286,660 | 9/1981 | Wagner et al. .................... 166/246 |
| 4,929,365 | 5/1990 | Clark et al. ....................... 435/262 |
| 4,954,258 | 9/1990 | Little ................................. 435/262 |
| 5,228,998 | 7/1993 | Di Clemente ..................... 210/747 |

OTHER PUBLICATIONS

Reed, G. 1982, Prescott & Dunn's Industrial Microbiology, 4th Ed, Avi Publishing Co., Inc., Westport, CN, p. 649.
Lide, Physical Constants of Organic Compounds, CRC Handbook of Chemistry and Physics, 1991–1992 72nd Edition, pp. 3–457.

*Primary Examiner*—Helen Pratt
*Attorney, Agent, or Firm*—Cushman Darby & Cushman IP Group of Pillsbury Madison & Sutro, LLP

[57] ABSTRACT

The present invention relates to a method of removing contaminating hydrocarbons from regions which are subjected to extreme temperatures. The temperatures are generally outside the range of optimum growth of hydrocarbon-degrading microorganisms. The method can involve the steps of contacting the region with hydrocarbon-degrading microorganisms, and adjusting the temperature of the region contacted with the microorganisms to optimize their growth.

17 Claims, 1 Drawing Sheet

METHOD OF ELIMINATING HYDROCARBONS CONTAMINATING A REGION SUBJECTED TO EXTREME TEMPERATURES

This application is a division of application Ser. No. 08/224,718 filed Apr. 8, 1994 now abandoned, which is a continuation-in-part of U.S. patent application Ser. No. 07/853,428, filed Mar. 18, 1992, now U.S. Pat. No. 5,346,929, which is a divisional of U.S. patent application Ser. No. 07/486,217, filed Feb. 28, 1990, which issued as U.S. Pat. No. 5,120,089 on Jun. 9, 1992, the entire disclosures of which are hereby incorporated by reference and relied upon.

BACKGROUND OF THE INVENTION

1. Field of the Invention

The present invention relates to a method of removing contaminating hydrocarbons from regions subjected to extreme temperatures.

2. Background Information

As the use and demand for hydrocarbon based fuels grow, the number of accidents involving hydrocarbon contamination of the environment also increases such as oil tankers spills and underground gasoline tank leakages. Spillage of hydrocarbons into waterways (and/or onto land) is a serious problem as it endangers plant and animal life.

The availability of hydrocarbon-degrading microorganisms has greatly increased the resources available for attacking hydrocarbon spills. Hydrocarbon-degrading microorganisms can be released at the site of a hydrocarbon spill in order to reduce the amount of contaminating hydrocarbon and thereby reduce the harm to the environment and its inhabitants.

In the case of a hydrocarbon spill in a region subjected to extreme temperatures, such as in the Alaskan oil spill, the problem in utilizing hydrocarbon-degrading microorganisms is that the temperature of the region is outside the range of temperatures in which the microorganisms grow. Without sufficient growth and division, microorganisms applied to the hydrocarbon spill will be ineffective in cleaning up the spill.

The present invention provides a significant advance in our ability to clean up hydrocarbon spills in regions subjected to extreme temperatures.

SUMMARY OF THE INVENTION

The present invention aims at overcoming the above-defined difficulties and accordingly, has an object to provide a method of eliminating hydrocarbons contaminating a region subjected to an extreme temperature.

It is another object of the present invention to provide a method of increasing the rate of growth of hydrocarbon-degrading microorganisms when in a region where the temperature is unfavorable for their growth.

Another object of the invention is to contain an oil spill in a water environment, e.g., ocean, lake, sea or river.

In one embodiment, the present invention relates to a method of eliminating hydrocarbons contaminating a region subjected to extreme temperatures comprising contacting the region with hydrocarbon-degrading microorganisms, and adjusting the temperature of the region contacted with the microorganisms to optimize growth of the microorganisms.

Various other objects and advantages of the present invention will become obvious from the following description of the invention.

All publications mentioned herein are hereby incorporated by reference.

DETAILED DESCRIPTION OF THE INVENTION

Figure 1:
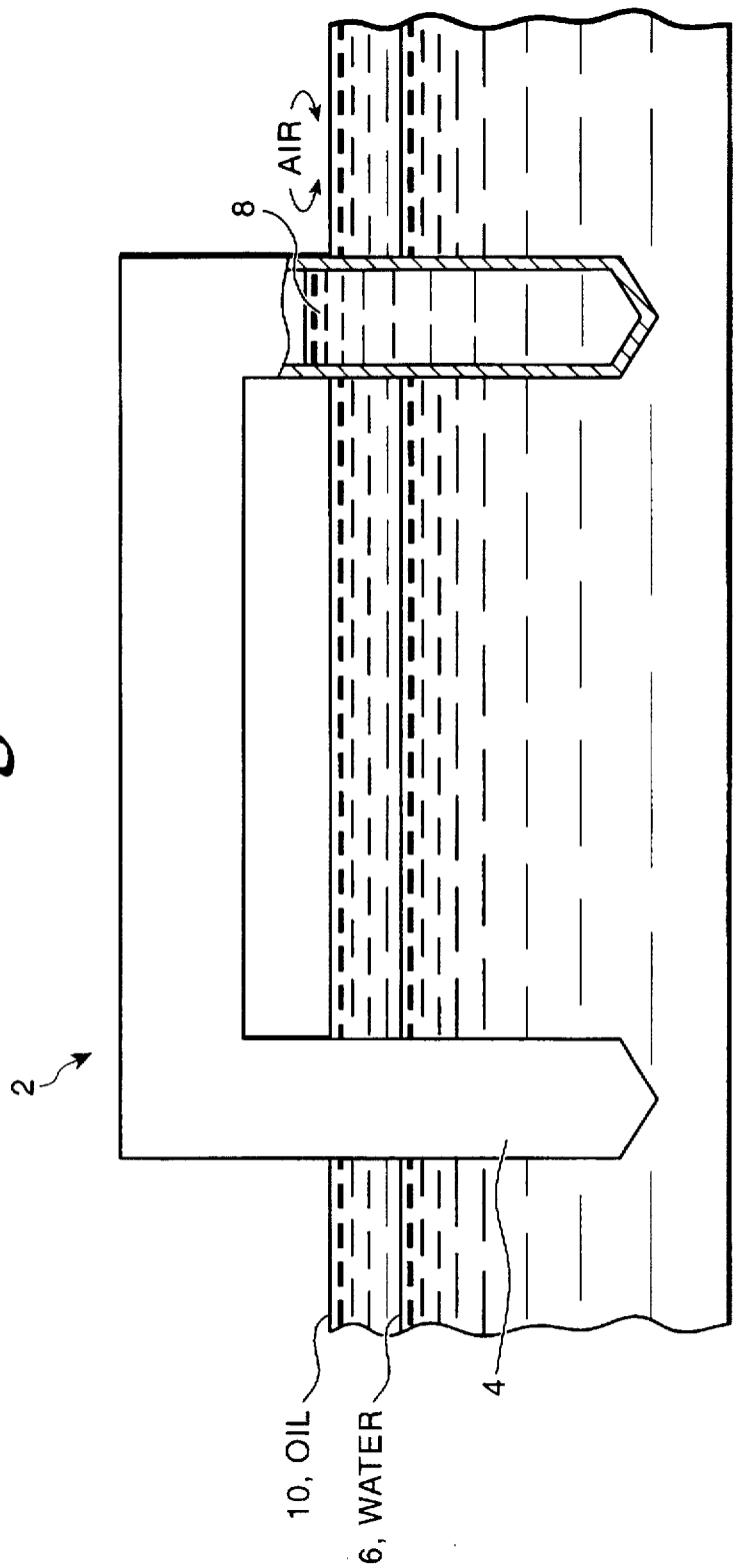
FIG. 1 shows a heat exchange apparatus floating in an oil spill. The level of heat exchange material within the apparatus is such that the apparatus floats and yet the apparatus extends below the oil spill so as to prevent the oil from spreading.

The present invention relates to a method of eliminating hydrocarbons, such as petroleum, contaminating a region subjected to extreme temperatures. The method comprises supplying hydrocarbon-degrading microorganisms and a heat exchange apparatus (see FIG. 1) containing a heat exchange material to the contamination site under conditions such that the microorganisms degrade the hydrocarbon contaminant.

The term "hydrocarbon" includes, but is not limited to, for example, petroleum hydrocarbon fuel oils, volatile liquid hydrocarbons, e.g., gasoline and kerosene, as well as heavier hydrocarbons.

The phrase "extreme temperature", as used herein, refers to a temperature at which the growth of most microorganisms is greatly reduced or completely inhibited.

Most of the microorganisms which eat the hydrocarbons have a preferred growth temperature of about 20° C.

The microorganisms of the present invention are hydrocarbon-degrading microorganisms such as bacterial and fungi which include, but are not limited to, the hydrocarbon-degrading microorganisms mentioned in the ATCC "Microbes and Cells at Work", 1st edition, 1988; ATCC Catalogue of Bacterial & Bacteriophages, 17th edition, 1989; Catalogue of Fungi/Yeasts, 17th edition, 1987, of the ATCC; and the December 1988 Supplement to the 1987 Fungi Catalogue. Microorganisms, as indicated in the above referenced catalogues, which degrade petroleum include *Acinetobacter calcoaceticus*, *Rhodococcus sp.* and *Candida utilis*. The entire disclosures of these four publications are hereby incorporated by reference and relied upon as are the references cited therein showing how to cultivate the microorganisms. Microorganisms which have been genetically altered to impart or enhance their hydrocarbon-degrading properties are also included within the scope of the present invention.

In one embodiment of the present invention, a hydrocarbon spill in an extremely cold region, such as Alaska, treated with hydrocarbon-degrading microorganisms is provided with a heat exchange apparatus containing a heat exchange material. The apparatus is placed at the site of the hydrocarbon spill, whether the hydrocarbon is contaminating water or land. The heat exchange apparatus encourages growth of the hydrocarbon-eating microorganisms applied to the hydrocarbon spill by regulating the temperature of its surroundings.

In another embodiment of the present invention, the heat exchange apparatus can be a single container or plurality of containers filled or partially filled with a heat exchange material which can be powered by motor battery. A group of containers can be connected to form a heat exchange raft of any desired design. The heat exchange apparatus can be moved to the spill site in the sea by ship, self propellation, or if not too large, dropped from an airplane.

In another embodiment of the present invention, an oil spill in a body of water is contained by surrounding the spill with a floatable (preferably heat exchange) apparatus 2 (see FIG. 1) that extends 4 into the water below the lower surface of the oil 6. The level of the heat exchange liquid, e.g., water in the heat exchanger, is shown at 8. The air-oil interface is shown at 10. A group of connected or disconnected containers comprising the heat exchange apparatus can encircle the oil spill and prevent further spread thereof.

In a specific embodiment of the present invention, the container can be made out of metal, such as iron, aluminum, magnesium, beryllium or an alloy, e.g., steel, or can be made of plastics, such as biaxially oriented polyethylene, polypropylene, ethylene-propylene copolymer, polystyrene, polyethylene terephthalate, poly-beta-hydroxybutyrate as well as other polymers disclosed in the applicant's U.S. application Ser. No. 07/213,342, filed on Jun. 30, 1988, now U.S. Pat. No. 4,952,426. If plastic containers are used, they can be made biodegradable, e.g., by using agents such as those mentioned in U.S. application Ser. No. 07/213,342, now U.S. Pat. No. 4,952,426. The plastic containers themselves can also be rendered biodegradable by incorporating microorganisms and/or starch or poly-beta-hydroxybutyrate or polylactylic lactic acid as mentioned in applicant's application "Biodegradable Plastic And Articles Made Therefrom", U.S. application Ser. No. 07/853,428, filed Mar. 18, 1992, now U.S. Pat. No. 5,346,929 the entire disclosure of which is hereby incorporated by reference. The plastic containers can also be degraded by incorporating ultraviolet high degraders, e.g., as set forth in Hudgin, U.S. Pat. No. 4,495,311. A combination of metal and plastic can also be used.

In another embodiment of the present invention, the heat exchange material can be a solid, liquid, gas or a mixture thereof. In any case, the amount of fluid or solid in the container should not be so great as to cause the container to sink if the container is to be used on a hydrocarbon spill in the open sea or lake or river. Of course, if the container is used on the shore or in shallow water, this is immaterial.

For use in cold regions, the preferred heat-exchange material is water, steam or a mixture of the two. The steam can be under pressure to get more into the container. Since it takes 540 calories to convert 1 gram of steam to water at 100° C. and only 80 calories to cool 1 gram of water from 100° C. to 20° C., the advantage of utilizing steam or super-heated steam to as great an extent as possible is apparent. A disadvantage of steam is the large volume of steam per unit of weight compared to water. Thus, a combination of water and steam in the container is the most desirable.

For use in warm regions, such as the tropics where it is necessary to reduce the temperature for optimum growth of the microorganism, the heat exchange apparatus is preferably filled with a cold liquid and/or solid, such as ice, ice-water mixture, or cold water.

The use of water and/or steam or water and/or ice has the advantage that if the container breaks, no further contaminants are introduced into the environment.

Once there is sufficient growth of the microorganisms, in many cases there will be generated sufficient heat in the destruction of the hydrocarbon that replacement of the heat exchange containers will not be necessary. This is similar to the way microorganisms generate heat in a compost pile. Until such internal heat is generated, the heat exchange apparatus is replaced when it no longer contains sufficient heat to efficiently regulate the temperature for the microorganisms.

If the heat exchanger is provided with a motor or battery, the heat exchanger material, e.g., water can be continuously or intermittently reheated as needed in cold regions, e.g., Alaskan waters.

It is also possible to provide the heat exchanger with an external coat containing the microorganism and a suitable growth medium, e.g., as mentioned in any of the four publications referred to above on page 11, in order to start or accelerate the process of decomposing the hydrocarbons.

If the container (preferably a heat exchanger) is intended to confine an oil spill, e.g., in the Gulf of Mexico, it should have a weight such that it will float, but be sufficient that the lower end of the container penetrates below the oil level. The container can be uncovered or desirably can have a cover so that rain water or waves do not form a water layer over the oil. The cover can be present originally or can be applied after the container is placed around the oil, e.g., a rolled-up cover could be unrolled by power means after the oil is surrounded. The confined oil can then be removed, e.g., by conventional means such as skimming.

It is understood that the examples and embodiments described herein are for illustrative purposes only and that various modifications or charges in light thereof will be suggested to persons skilled in the art and are to be included within the spirit and preview of the present application and scope of the appended claims.

I claim:

1. A method of eliminating hydrocarbons in an oil spill contaminating a region subjected to extreme temperatures outside the optimum growth of hydrocarbon-degrading microorganisms, comprising the steps of:
   (i) contacting said region with hydrocarbon-degrading microorganisms, and (ii) adjusting the temperature of the region contacted with the microorganisms to optimum growth of said microorganisms, wherein said temperature is adjusted with a heat-exchange apparatus comprising a heat-exchange material.

2. The method according to claim 1, wherein said hydrocarbon-degrading microorganisms are at least one of bacteria or fungi.

3. The method according to claim 1, wherein said heat exchange material comprises a liquid or solid or combination thereof.

4. The method according to claim 1, wherein said heat exchange material is a form of water.

5. The method of claim 1, wherein the region is a body of water.

6. The method according to claim 1 wherein the heat exchanger apparatus is a heat exchanger having an external coating comprising hydrocarbon eating microorganisms.

7. The method according to claim 6 wherein the coating includes an organic growth medium for the microorganisms.

8. The method according to claim 7 wherein said hydrocarbon-degrading microorganisms are at least one of bacteria or fungi.

9. The method according to claim 6 wherein said heat exchange material comprises liquid or solid or combination thereof.

10. The method according to claim 9 wherein the coating includes an organic growth medium for the microorganisms.

11. The method according to claim 6 wherein said heat exchange material is a form of water.

12. The method according to claim 11 wherein the coating includes an organic growth medium for the microorganisms.

13. A method according to claim 1 wherein said heat exchange material comprises steam.

14. The method according to claim 1, wherein the hydrocarbons comprise at least one of hydrocarbon oil, volatile liquid hydrocarbons and heavier hydrocarbons.

15. The method according to claim 1, wherein the hydrocarbons comprise hydrocarbon oil.

16. The method according to claim 1, wherein said heat exchange material is a mixture of steam and water.

17. The method according to claim 1 wherein said oil spill contaminates (a) an ocean, sea, lake or river or (b) land.

* * * * *